United States Patent [19]
Dodick

[11] Patent Number: 5,324,282
[45] Date of Patent: Jun. 28, 1994

[54] SURGICAL INSTRUMENT WITH INPUT POWER TRANSDUCER

[76] Inventor: Jack M. Dodick, 535 Park Ave., New York, N.Y. 10021

[21] Appl. No.: 844,661

[22] PCT Filed: Oct 24, 1990

[86] PCT No.: PCT/US90/06109

§ 371 Date: Apr. 8, 1992

§ 102(e) Date: Apr. 8, 1992

[87] PCT Pub. No.: WO91/06271

PCT Pub. Date: May 16, 1991

Related U.S. Application Data

[63] Continuation-in-part of Ser. No. 426,971, Oct. 25, 1989, abandoned, and a continuation-in-part of Ser. No. 429,141, Oct. 30, 1989, abandoned.

[51] Int. Cl.$^5$ .............................................. A61N 5/06
[52] U.S. Cl. ........................................ 606/15; 606/2; 606/6; 606/10; 128/897; 601/2
[58] Field of Search ................. 128/24 AA, 345, 397, 128/398, 898, 897; 606/2-7, 10-19, 127, 128

[56] References Cited

U.S. PATENT DOCUMENTS 5,041,121  8/1991  Wondrazek et al. ................. 606/15

FOREIGN PATENT DOCUMENTS 8804540  6/1988  European Pat. Off. .
3842916  2/1990  Fed. Rep. of Germany .

Primary Examiner—David M. Shay
Attorney, Agent, or Firm—McAaulay Fisher Nissen Goldberg & Kiel

[57] ABSTRACT

A surgical instrument in the form of, for example, a two mm needle has an open distal aspiration port for holding tissue to be fractured. An optical fiber extends along the length of the needle and has it's distal end positioned close to a metal target. Pulses of laser energy are discharged from the distal end of the optical fiber to strike the target. The target acts as a transducer converting the electromagnetic energy to shockwaves that are directed onto tissue in an operating zone adjacent to the aspiration port. The mechanical shockwaves cause the tissue to fracture and the tissue, together with the irrigating fluid is drawn out through an aspirating passageway. A flexible as the needle enhances access to various area where tissue is to be fractured.

9 Claims, 2 Drawing Sheets

SURGICAL INSTRUMENT WITH INPUT POWER TRANSDUCER

REFERENCE TO RELATED APPLICATIONS

This application is a continuation-in-part of co-pending patent applications filed by applicant in the United States Patent Office as Ser. No. 426,971 on Oct. 25, 1989, entitled Laser Powered Surgical Instrument; and as Ser. No. 429,141 on Oct. 30, 1989 entitled Surgical Instrument With Input Power Collector.

BACKGROUND OF THE INVENTION

In general this invention relates to a laser powered surgical instrument and more particularly to one that provides an efficient and safe means for delivering laser energy to tissue for the purpose of operating on the tissue.

The operating instrument of this invention will be described in connection with an embodiment adapted to be used in eye surgery and particularly for cataract removal. However, the invention can be embodied in devices which are adapted to other surgical purposes.

The use of laser energy to perform eye surgery is well known. There are a large number of known devices and patents which are relevant to this art.

One recent patent is the Eichenbaum U.S. Pat. No. 4,698,828 which contains an adequate description of the background in this art and contains a reference to a number of relevant patents. In addition, a useful text that describes both principles and applications of laser surgery in Ophthalmology is the text *The Nd-YAG Laser In Ophthalmology* by Roger F. Steinert and Carmen A. Puliafito, published by W. B. Saunders Company in 1985; ISBN O-7216-1320-9.

The desired parameters for a laser operated surgical device are the requirement of efficiency and small size coupled with avoiding damage to adjacent areas of the tissue being operated on. Enhanced safety for the operator as well as safety for the patient by minimizing exposure to laser light are goals of any design for such an instrument. The small size provides the advantage of making it possible to operate through a very small incision; a three millimeter incision being a goal in cataract surgery. Efficiency of operation serves the advantages of (a) keeping down the overall weight, cost and size of the instrument (b) minimizing the amount of heat or other energy transmitted to adjacent tissue and (c) assuring maximum effect on the tissue to be severed.

Accordingly, the major purpose of this invention is to provide a surgical instrument meeting the above requirements. A related purpose is to provide such an instrument that generates a minimum of heat and has the least possible impact on tissue other than the tissue to be operated on.

Trauma to the patient is reduced by providing minimum size incisions and delivering the minimum amount of energy to the patient consistent with performing the operation involved. Trauma is minimized by developing as little heat as possible and avoiding loss or scattering of radiant energy into the patient's tissue other than at the desired site of the operation. Thus, safety, comfort and minimum trauma consistent with performing the operation is a goal of any such surgical instrument.

More particularly, from the point of view of minimizing trauma, enhancing safety and minimizing size of surgical instrument, it is important to provide as efficient an operating instrument as possible. The efficiency desired is one in which the maximum percentage of input energy is delivered to the tissue to be fractured or emulsified. Manifestly, the greater the percentage of input energy that is delivered to the tissue to be operated on, the less energy will be delivered to other tissue and, in general, the smaller the operating instrument can be. Thus a goal of this invention is to provide a surgical instrument in which a high fraction of energy is delivered to the tissue to be operated on.

BRIEF DESCRIPTION

In brief, one embodiment of this invention is a surgical instrument using neodymium-YAG laser to provide light energy at a wavelength of 1,064 nano-meters. This light energy is delivered to the body site in pulses, each pulse having a pulse width of approximately eight nano-seconds.

The surgical instrument is a needle which is essentially an elongated small diameter (approx. 2.0 mm) tubular device. Within the needle, there is an optical fiber element suitable for carrying the pulses of laser energy. The distal end of the needle is partly covered by a metal target and is partly open. The open portion forms an aspiration port. The distal end of the fiber is approximately 2.0 mm from the target. The needle may have an irrigating passageway along the inner wall of the needle.

In use, the distal end of the needle is placed adjacent to the tissue to be removed. A vacuum is applied so that the tissue is pulled against or into the aspiration port. Laser energy is fed down the fiber as very short duration, high repetition rate pulses of energy. This energy is discharged at the distal end of the fiber and strikes the metal target to generate shockwaves in the fluid media adjacent to the target. This shockwaves fracture the tissue which is being held by the vacuum in the zone adjacent to the port. The tissue thus fractured is aspirated out in small pieces and the successive pulses of laser energy create successive shockwaves that fracture off successive bits of tissue. Saline provided by an irrigating tube aids in flushing out the tissue particles thus fractured.

The target reduces the threshold of optical breakdown making it possible to produce shockwaves with lower energy pulses than without the target. The target is configured and positioned to direct the shockwaves against the tissue to be fractured. The target also provides a shield which protects surrounding tissue from both laser light and from the shockwaves.

The manner in which the tissue is surgically severed is through the effect of a series of high energy small duration shockwaves which serve to shatter the tissue on which the shockwaves impinge. It is believed that this is the primary mechanism by which the device of this invention achieves its result. The amount of light energy which is converted to heat is sufficiently small so that the heat energy is not believed to have a significant role in this surgical operation.

DESCRIPTION OF THE PREFERRED EMBODIMENTS

The embodiments shown are similar in many respects and thus the same reference numbers are used for the same part in various embodiments.

Figure 1:
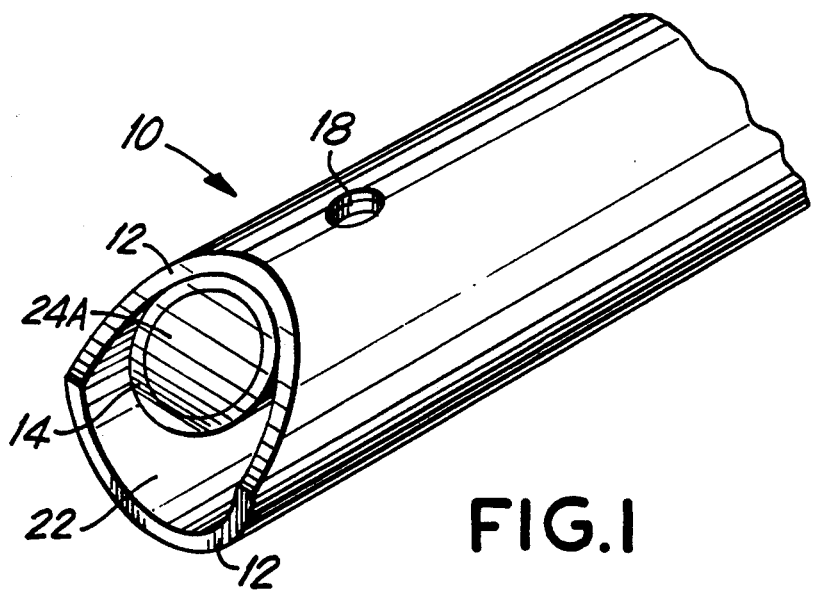
FIG. 1 is a perspective view of the distal end of the needle-like probe which illustrates one embodiment of the device of this invention.
Figure 2:
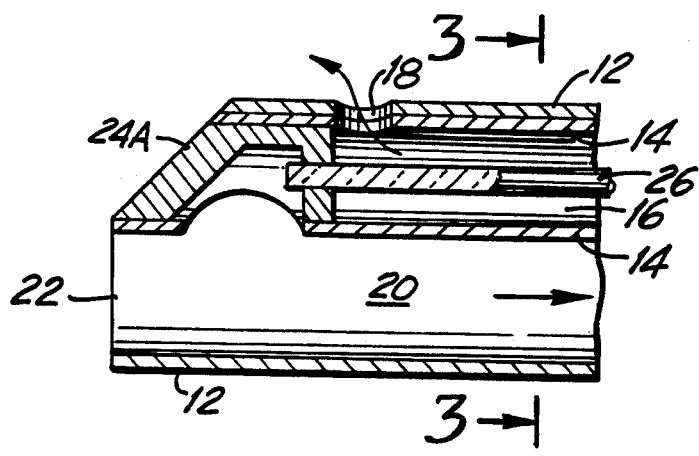
FIG. 2 is a longitudinal cross-section through the FIG. 1 operating instrument.
Figure 3:
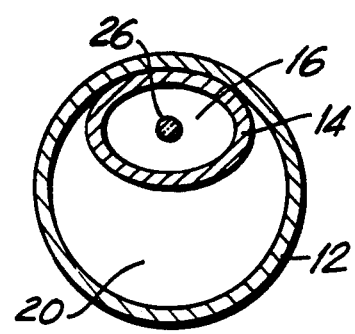
FIG. 3 is a cross-sectional view taken along the plane 3—3 of FIG. 2.

As shown in FIGS. 1 through 4, the probe 10 is a needle like distal end of the operating instrument. The probe 10 has a tubular outside wall 12 having an outer diameter of for example two millimeters (2 mm) and a wall thickness of approximately 0.2 mm. Within the outer tubular wall 12 there is an inner tubular wall 14, also having a wall thickness of about 0.2 mm. The tube 14 is preferably oval as best seen in FIG. 3. The passageway 16 within the inner tubular wall 14 is one through which an irrigating fluid such as a saline solution is administered and is applied to the tissue being operated on through the sidewall port 18. The passageway 20 between the outer wall 12 and the inner wall 14 is an aspirating passageway 20. Vacuum applied to this aspirating passageway 20 serves to draw tissue in through the front port 22.

Figure 4:
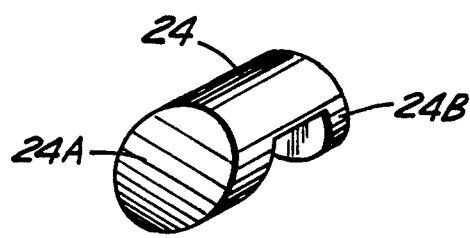
FIG. 4 is a perspective view of the insert used to provide the target in the FIG. 1 embodiment.

A titanium insert 24 is wedged into the distal end of the inner tubular wall. FIG. 4 shows the insert 24 for the FIG. 1 embodiment. This titanium 24 insert has a target portion 24A which serves, as described below, as a target plate for laser energy. A stem portion 24B has an opening through which an optical fiber element 26 extends.

Tissue which is drawn against the port 22 by vacuum is fractured by shockwaves generated when laser energy emitted from the distal end of the optical fiber 26 impinges upon the inner surface of the target 24A. The shockwaves generated are transmitted through the fluid media to impinge on and fracture the tissue held in the tissue receiving zone adjacent to the port 22. This fractured tissue, together with the irrigating fluid, is aspirated out through the aspiration passageway 20.

A plastic layer on the outside of the insert 24 may be useful to minimize transmission of shockwaves through the distal end of the instrument to tissue adjacent the instrument. The plastic material can be one of those proven to be useable in eyes without serious side results such as the plastic used in eye implants. Such plastics used today include the polytetrafluoride resin also known as PTF resin and sold under the trademark Teflon. A plastic sold under the trademark Perspex can also be used. The plastic layer can be adhered to the distal end of the instrument by known techniques.

The optical fiber 26 has a 300 micro-meter (0.3 mm) diameter core encased in cladding. The optical fiber 26 together with its cladding is a known type of optical fiber and need not be discussed in detail herein. The distal end of the optical fiber 26 is approximately 2 mm from the inner surface of the target 24A.

The irrigating passageway 16 provides liquid at the port 18 at the distal end 10 of the instrument to irrigate the field of the operation. This liquid also maintains the pressure in the eye where the device is used for cataract surgery. This liquid is necessary to aspirate out the fractured tissue through the aspirating passageway 20.

Figure 8:
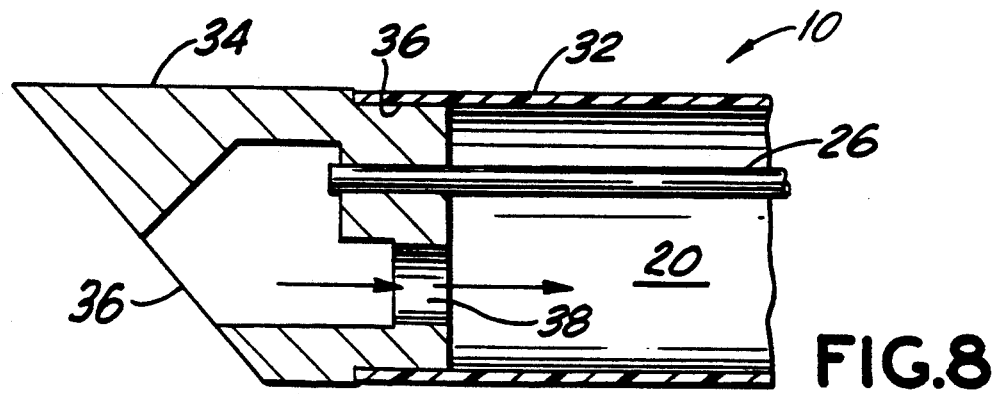
FIG. 8 is a longitudinal cross-section of the distal end of a third embodiment of the invention illustrating a flexible needle as the probe and in which the irrigating passageway is omitted.

FIG. 8 illustrates an embodiment where there is no irrigating passageway in the instrument. Irrigation can be provided by known techniques through use of a standard irrigating tubular instrument. One advantage of the FIG. 8 design is that it makes possible a smaller diameter instrument than one which requires the irrigating passageway 16.

In operation, pulses of laser energy are transmitted down the optical fiber 26. The target 24A drops the threshold of optical breakdown and permits the use of lower energy levels than would otherwise be required. Thus pulses of appropriate energy are emitted from the distal end of the optical fiber 26 to strike the target 24A and generate mechanical shockwaves in the fluid media adjacent to the inner surface of the target. The shockwaves are directed by the target 24A toward the tissue which is held at the port 22 by the vacuum applied to the passageway 20. The shockwaves cause the tissue to fracture into small pieces which are then sucked out through the aspirating passageway 20.

The target 24A also serves to protect the surrounding tissue from laser energy. Thus the only tissue exposed to either laser energy or shockwaves is that tissue in the tissue receiving zone adjacent to the port 22. Thus the target functions as a laser light shield.

Because the target is both the target and the shield, its optimum configuration will have to be determined by experimentation to provide the optimum trade-off between effective shielding of tissue from laser energy and effective transmission of shockwaves onto the tissue to be fractured.

If particles of fractured tissue get struck in the aspirating passageway 20, then by a known technique of reversing the aspirating pump, a metered positive pressure pulse is used to dislodge the stuck particle.

In one embodiment, a neodymium-YAG Q switched laser generator 30 is employed thereby providing laser energy having a wavelength of 1,064 nano-meters. In that embodiment, the laser energy is provided in pulses having a duration of eight (8) nano-seconds and a pulse repetition rate of twenty (20) pulses per second. The energy provided is 100 milli-joules per second and thus the energy of each pulse is five (5) milli-joules. That particular embodiment is intended for removing a cataract in eye surgery.

The embodiment shown in 5 and 6 illustrates an embodiment that is presently preferred over that shown in FIGS. 1 through 4. This FIG. 5 embodiment primarily differs from the FIG. 1 embodiment in that the distal end of the probe 10 is a plane at an angle of forty-five degrees (45°) to the horizontal and provides a port 22a which more optimally positions the tissue to receive the shockwaves generated off the inner surface of the titanium insert 24a. The titanium insert 24a has a stepped down zone at its proximal end (in the stem portion) to permit being fit into the distal end of the stainless steel irrigating tube 14a. In addition, the titanium insert 24a is held in place on the stainless steel outer tube 12a by spot welding which creates enough of a surface engagement to hold the titanium insert in place for purposes of an operating device.

Figure 6:
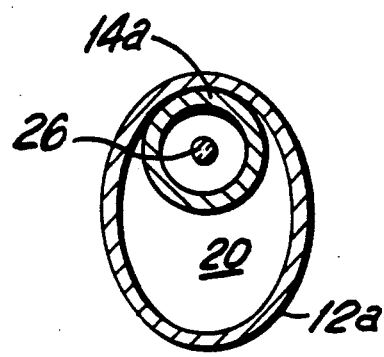
FIG. 6 is a cross-section view taken along the plane 6—6 of FIG. 5.
Figure 7:
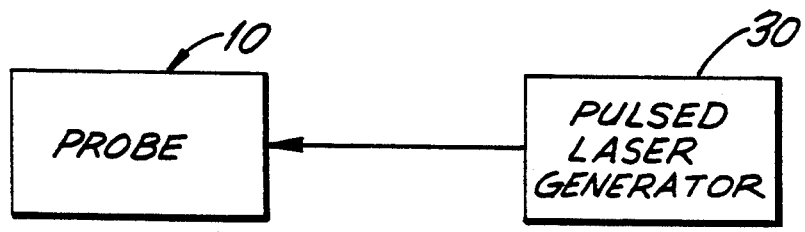
FIG. 7 is a block diagram illustrating the use of a pulsed laser generator is to provide the input energy to the fiber optic element.

As shown in FIG. 6, the outer tube 12a is preferable elliptical and the inner tube 14a is circular. The value of an elliptical or oval needle 10 is that it provides for a more desirable insertion dimension of the wound required to pass the oval operating needle into the eye.

Figure 5:
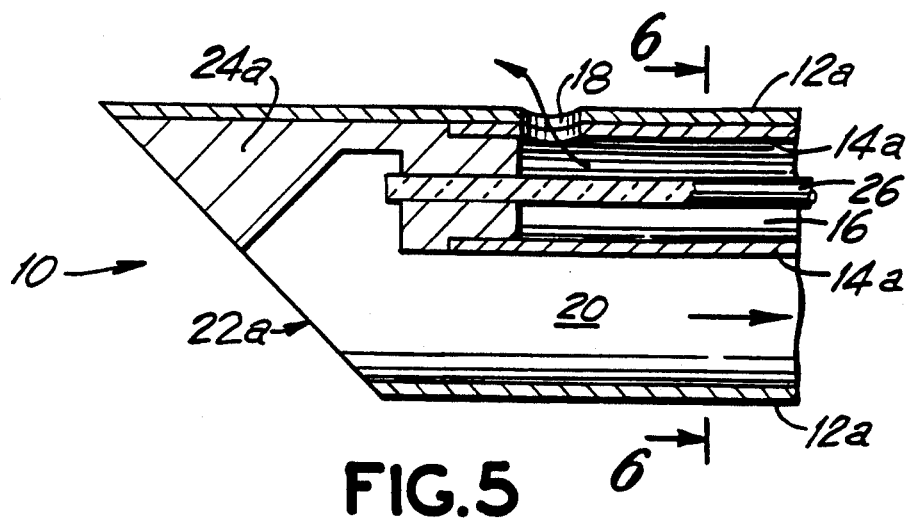
FIG. 5 is a perspective view of the distal end of a second embodiment of the device of this invention.

The embodiment shown in FIGS. 5 and 6 represents the most recently constructed and tested embodiment. In the sample of that embodiment that was constructed and tested, the tubes 12a and 14b are stainless steel tubes. The following are the approximate dimensions of that sample. The outer tube 12a has outer dimensions of 2.16 mm by 1.37 mm (85 mils by 54 mils) and a wall thickness of 0.1 mm (4.5 mils) The irrigating tube 14a has a outer diameter of 1.1 mm (43 mils) and a wall thickness of 0.09 mm (3.5 mils). The port 18 has a diameter of 0.69 mm (27 mils) and the distal edge of the port is located 3.8mm (150 mils) from the distal tip of the probe 10. The titanium insert 24a has a diameter of 1.1 mm (43 mils) and is necked down in the stem to be fitted into the irrigating tube 14a. The necked down zone has a length of 0.89 mm (35 mils) while the overall length of the stem of the insert in which this necked down zone is contained is 1.19 mm (47 mils). The opening in the stem of the insert 24a that accommodates the optical fiber 26 is 0.5 mm (20 mils) so as to provide a slip fit relationship for the fiber 26. This fiber 26 has a diameter of 0.45 mm (17 to 18 mils). The neck that connects the distal triangular target portion with the proximal stem has a width of 0.36 mm (14 mils). The distal or front wall of the insert 24a is a plane that is at an angle of forty five degrees (45) to the axis of the probe 10. The target wall is perpendicular to the exterior or distal wall of the insert.

FIG. 8 shows a design for a flexible needle. A thin wall flexible plastic tubing 32 such as Teflon has an outer diameter of 2 mm and a wall thickness somewhere between 0.1 and 0.5 mm. This tubing 32 is heat shrunk onto the titanium insert 34. The titanium insert 34 contains a necked down zone 36 onto which the tubing 32 is shrunk. The outer surface of the necked down zone 36 preferably has a series of sharp protuberances which will engage the end of the tubing 32 when the tubing is shrunk onto the necked down zone therefore positively holding the tubing onto the insert. This might prove to be important to assure that the shockwaves generated do not drive or pull the insert 34 out of the tubing 32. The FIG. 8 embodiment omits the irrigating passageway thereby making possible a smaller diameter probe 10. Irrigation is provided by a known technique using a separate irrigating tube.

Otherwise, the FIG. 8 arrangement is similar to the arrangement shown in FIG. 5. In particular, the optical fiber 26 is mounted in the insert 34 and has a distal end spaced from the target face of the insert. The result is that shockwaves are reflected down toward a tissue receiving zone inside the instrument and adjacent to the port 36. An opening 38 through the insert 34 is made as large as possible in order to provide a reasonable opening through which fractured tissue is aspirated out the aspirating passageway 20.

Such a flexible operating instrument will permit ready access by the surgeon to all portions of the capsular bag in a cataract operation. The limit on the radius of curvature of such an instrument will be determined by the optical fiber. It is believed that a radius of curvature as little as three (3)mm might be achieved in such a design.

A flexible probe might well be controlled by a guide wire similar to that used in endoscopic controls. This would permit the surgeon to move the port 36 of the probe to any part of the capsular bag. This would allow complete evacuation of the capsular bag through a small opening and allow for refilling of the capsular bag with an optically qualified compound such as silicone.

Although certain embodiments of the invention have been shown, there are variations in the structure shown which applicant contemplates as potentially useful. These variations are not necessarily shown. They would be understood to one skilled in the art.

For example, the thickness of the titanium target can be adjusted so as to extend the life of the instrument.

The titanium gradually deteriorates in response to each pulsing of the target. A given titanium target may operate for about ten thousand pulses. Eight thousand pulses are often required for a single operation. Experience may call for adjusting the thickness of the target to affect target life.

As another example, the material of the target might be selected to be some other material that is relatively inactive chemically such as the various noble metals.

In addition, the outer surface of the titanium insert 24, 24a, 34 might be rounded to assure that any energy transmitted through the target is not concentrated along a line or at a point.

The use of a separate irrigating tube and the elimination of the irrigating passageway in the probe can be a design feature of a rigid probe as well as of a flexible probe.

What is claimed is:

1. A surgical needle for fracturing tissue comprising:
    a tubular sidewall having a longitudinal axis and a distal end portion,
    a laser fiber extending longitudinally to said distal end portion of said sidewall, said laser fiber having a longitudinal axis and a distal end,
    a target mounted adjacent to said distal end of said laser fiber,
    said target being aligned with said distal end of said laser fiber to receive laser energy from said laser fiber,
    means to produce laser pulses of sufficient energy to produce optical breakdown at the target material,
    said distal end portion of said sidewall in communication with a tissue receiving port and a tissue receiving zone adjacent to said port,
    said tissue receiving port and said tissue receiving zone being radially displaced from said longitudinal axis of said laser fiber,
    said optical breakdown at said target producing shockwaves that are propagated to said tissue receiving zone,
    laser energy from said laser fiber having a path that is displaced from said tissue receiving zone, and
    an aspirating passageway extending longitudinally within said sidewall and in communication with said tissue receiving zone.

2. The surgical needle of claim 1 wherein said tubular sidewall has a distal endwall and said target comprises at least a portion of said endwall.

3. The surgical instrumentation for fracturing tissue comprising:
    the surgical needle of claim 1, and
    generation means coupled to said laser fiber to provide pulsed laser energy to said fiber.

4. The surgical needle of claim 1 wherein said sidewall is flexible.

5. The surgical needle of claim 1 further comprising:
an irrigating passageway within said tubular sidewall,
said tubular sidewall having an irrigating port in communication with said irrigating passageway,
fluid from said irrigating passageway passing through said irrigating port to irrigate any tissue at said tissue receiving port and assist aspiration of fractured tissue through said aspirating passageway.

6. The surgical needle of claim 5 wherein said tubular sidewall has a distal endwall and said target comprises at least a portion of said endwall.

7. The surgical instrumentation for fracturing tissue comprising:
the surgical needle of claim 5, and
generation means coupled to said laser fiber to provide pulsed laser energy to said fiber.

8. The surgical needle of claim 5 wherein said sidewall is flexible.

9. The method of surgically removing tissue comprising the steps of:
drawing tissue into a tissue receiving zone of a surgical needle,
providing pulses of laser energy of sufficient energy to produce optical breakdown of the material of a target,
directing said pulses of laser energy along a path displaced from said tissue receiving zone onto said target adjacent to and displaced from said tissue receiving zone to convert said laser energy into mechanical shockwaves,
propagating said mechanical shockwaves to the tissue to be fractured in said tissue receiving zone and thereby fracturing the tissue,
aspirating the fractured tissue out of an aspirating passageway in communication with said tissue receiving zone, and
providing irrigation to an area outside said surgical needle to assist said step of aspirating.

* * * * *